(12) United States Patent　　(10) Patent No.:　US 12,638,460 B2
Majd et al.　　(45) Date of Patent:　May 26, 2026

(54) METHOD FOR NASH RISK ASSESSMENT

(71) Applicant: GENFIT, Loos (FR)

(72) Inventors: Zouher Majd, Ennetieres-En-Weppes (FR); Pierre Chaumat, Fontainebleau (FR)

(73) Assignee: GENFIT, Loos (FR)

( * ) Notice: Subject to any disclaimer, the term of this patent is extended or adjusted under 35 U.S.C. 154(b) by 664 days.

(21) Appl. No.: 18/019,488

(22) PCT Filed: Aug. 2, 2021

(86) PCT No.: PCT/EP2021/071548
§ 371 (c)(1),
(2) Date: Feb. 3, 2023

(87) PCT Pub. No.: WO2022/029066
PCT Pub. Date: Feb. 10, 2022

(65) Prior Publication Data
US 2023/0296624 A1　　Sep. 21, 2023

(30) Foreign Application Priority Data

Aug. 3, 2020　(EP) .................................... 20305895

(51) Int. Cl.
*G01N 33/68*　　(2006.01)
(52) U.S. Cl.
CPC ... *G01N 33/6893* (2013.01); *G01N 2800/085* (2013.01); *G01N 2800/56* (2013.01)
(58) Field of Classification Search
CPC ......... G01N 2800/085; G01N 2800/56; G01N 2800/7052; G01N 33/6893
See application file for complete search history.

(56) References Cited

U.S. PATENT DOCUMENTS

| | | | |
|---|---|---|---|
| 2014/0179806 A1* | 6/2014 | Kain ................ | G01N 33/56916 |
| | | | 435/5 |
| 2015/0377909 A1* | 12/2015 | Cavet ..................... | G16B 40/00 |
| | | | 702/19 |
| 2016/0139149 A1 | 5/2016 | Elias et al. | |
| 2020/0216901 A1 | 7/2020 | Hanf et al. | |
| 2020/0340060 A1* | 10/2020 | Billin ................. | G01N 33/6893 |

FOREIGN PATENT DOCUMENTS

| | | | | |
|---|---|---|---|---|
| CN | 111 197 040 | 5/2020 | | |
| WO | WO 2012/105590 | 8/2012 | | |
| WO | WO-2016179469 A1 * | 11/2016 | .......... | C12Q 1/6883 |
| WO | WO 2019/038456 | 2/2019 | | |
| WO | WO 2019/217450 | 11/2019 | | |

OTHER PUBLICATIONS

Written Opinion in International Application No. PCT/EP2021/071548, Nov. 9, 2021, pp. 1-10.
Piazzolla, V. A. et al. "Noninvasive Diagnosis of NAFLD and NASH" Cells, Apr. 17, 2020, pp. 1-17, vol. 9, No. 1005.

* cited by examiner

*Primary Examiner* — Jennifer Wecker
(74) *Attorney, Agent, or Firm* — SALIWANCHIK, LLOYD & EISENSCHENK

(57) ABSTRACT

The present invention relates to a new assay to diagnose nonalcoholic steatohepatitis (NASH), NASH progression and NASH fibrosis stage.

Figure 1:
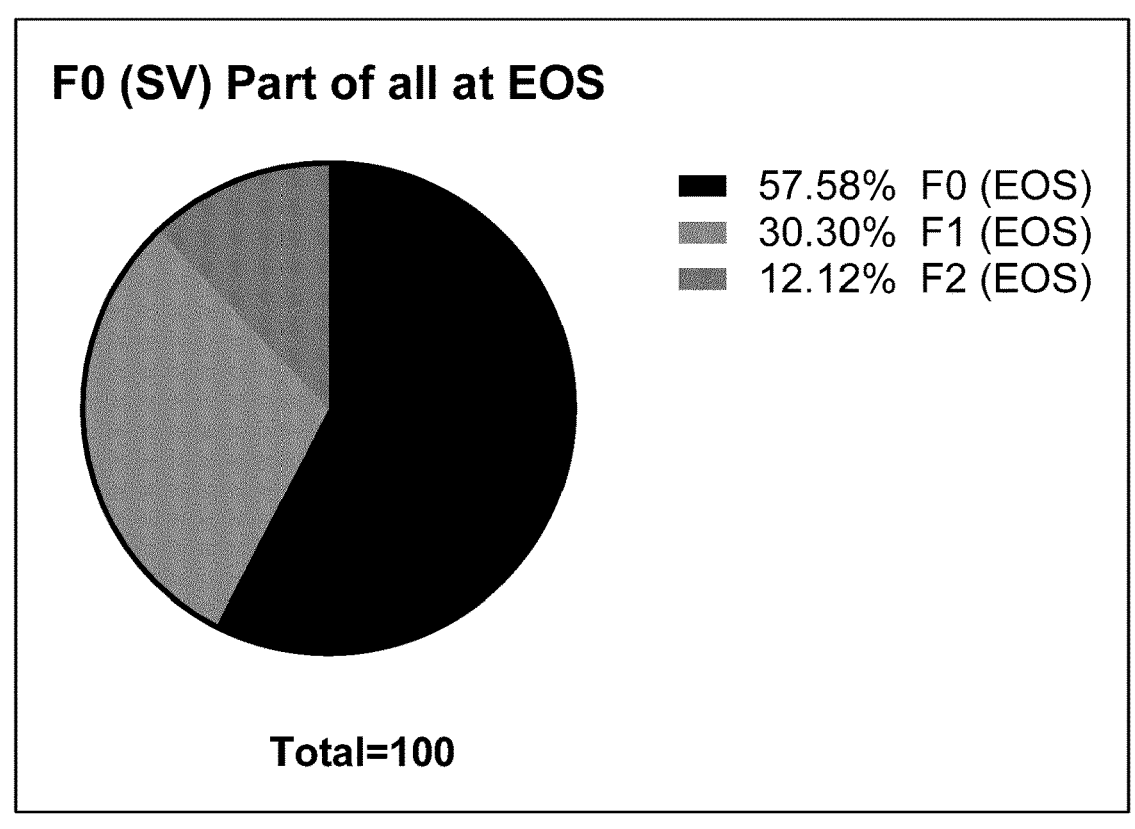

6 Claims, 2 Drawing Sheets
Specification includes a Sequence Listing.

F0 (SV) Part of all at EOS

■ 57.58% F0 (EOS)
▨ 30.30% F1 (EOS)
▨ 12.12% F2 (EOS)

Total=100

SEQUENCE LISTING

<160> NUMBER OF SEQ ID NOS: 1

<210> SEQ ID NO 1
<211> LENGTH: 383

<212> TYPE: PRT
<213> ORGANISM: homo sapiens

<400> SEQUENCE: 1

Met Gly Val Lys Ala Ser Gln Thr Gly Phe Val Val Leu Val Leu Leu
1               5                   10                  15

Gln Cys Cys Ser Ala Tyr Lys Leu Val Cys Tyr Tyr Thr Ser Trp Ser
            20                  25                  30

Gln Tyr Arg Glu Gly Asp Gly Ser Cys Phe Pro Asp Ala Leu Asp Arg
        35                  40                  45

Phe Leu Cys Thr His Ile Ile Tyr Ser Phe Ala Asn Ile Ser Asn Asp
    50                  55                  60

His Ile Asp Thr Trp Glu Trp Asn Asp Val Thr Leu Tyr Gly Met Leu
65                  70                  75                  80

Asn Thr Leu Lys Asn Arg Asn Pro Asn Leu Lys Thr Leu Leu Ser Val
                85                  90                  95

Gly Gly Trp Asn Phe Gly Ser Gln Arg Phe Ser Lys Ile Ala Ser Asn
            100                 105                 110

Thr Gln Ser Arg Arg Thr Phe Ile Lys Ser Val Pro Pro Phe Leu Arg
        115                 120                 125

Thr His Gly Phe Asp Gly Leu Asp Leu Ala Trp Leu Tyr Pro Gly Arg
        130                 135                 140

Arg Asp Lys Gln His Phe Thr Thr Leu Ile Lys Glu Met Lys Ala Glu
145                 150                 155                 160

Phe Ile Lys Glu Ala Gln Pro Gly Lys Lys Gln Leu Leu Leu Ser Ala
            165                 170                 175

Ala Leu Ser Ala Gly Lys Val Thr Ile Asp Ser Ser Tyr Asp Ile Ala
            180                 185                 190

Lys Ile Ser Gln His Leu Asp Phe Ile Ser Ile Met Thr Tyr Asp Phe
            195                 200                 205

His Gly Ala Trp Arg Gly Thr Thr Gly His His Ser Pro Leu Phe Arg
        210                 215                 220

Gly Gln Glu Asp Ala Ser Pro Asp Arg Phe Ser Asn Thr Asp Tyr Ala
225                 230                 235                 240

Val Gly Tyr Met Leu Arg Leu Gly Ala Pro Ala Ser Lys Leu Val Met
            245                 250                 255

Gly Ile Pro Thr Phe Gly Arg Ser Phe Thr Leu Ala Ser Ser Glu Thr
            260                 265                 270

Gly Val Gly Ala Pro Ile Ser Gly Pro Gly Ile Pro Gly Arg Phe Thr
            275                 280                 285

Lys Glu Ala Gly Thr Leu Ala Tyr Tyr Glu Ile Cys Asp Phe Leu Arg
        290                 295                 300

Gly Ala Thr Val His Arg Ile Leu Gly Gln Gln Val Pro Tyr Ala Thr
305                 310                 315                 320

Lys Gly Asn Gln Trp Val Gly Tyr Asp Asp Gln Glu Ser Val Lys Ser
            325                 330                 335

Lys Val Gln Tyr Leu Lys Asp Arg Gln Leu Ala Gly Ala Met Val Trp
            340                 345                 350

Ala Leu Asp Leu Asp Asp Phe Gln Gly Ser Phe Cys Gly Gln Asp Leu
            355                 360                 365

Arg Phe Pro Leu Thr Asn Ala Ile Lys Asp Ala Leu Ala Ala Thr
        370                 375                 380

METHOD FOR NASH RISK ASSESSMENT

CROSS-REFERENCE TO RELATED APPLICATION

This application is the U.S. national stage application of International Patent Application No. PCT/EP2021/071548, filed Aug. 2, 2021.

REFERENCE TO SEQUENCE LISTING

The Sequence Listing for this application is labeled "Seq-List.txt" which was created on Jan. 20, 2023 and is 3,498 bytes. The entire content of the sequence listing is incorporated herein by reference in its entirety.

The present invention relates to a new assay to diagnose nonalcoholic steatohepatitis (NASH) progression in nonalcoholic fatty liver disease (NAFLD) patients.

BACKGROUND OF THE INVENTION

NAFLD is the most common liver disease worldwide. It refers to a group of conditions where there is accumulation of excess fat in the liver of subjects who drink little or no alcohol. A group of subjects with NAFLD has a more serious condition called nonalcoholic steatohepatitis (NASH). In NASH, fat accumulation is associated with liver cell inflammation. NASH is a serious condition that may lead to severe liver scarring and cirrhosis, hepatocellular carcinoma and liver-related death. Cirrhosis occurs when the liver sustains substantial damage, and the liver cells are gradually replaced by scar tissue, which results in the inability of the liver to work properly. Some patients who develop cirrhosis may eventually require a liver transplant.

NAFLD is diagnosed by detecting the presence of fat accumulation into the liver using ultrasound techniques. The evaluation and follow up of NASH with fibrosis have been traditionally performed by liver biopsy. However, the place of liver biopsy as the standard of reference has been challenged by the increasing awareness of a number of drawbacks related to its use (invasiveness, sampling error, inter/intraobserver variability). New non-invasive diagnostic methods dedicated to the identification of patients at risk of NASH progression are needed.

Existing CHI3L1 assays do not allow to diagnose, to stratify and/or to assess risk of NASH progression in NAFLD patients. The present invention provides such non-invasive methods, based on the determination of CHI3L1 levels in a blood, serum or plasma sample and their comparison to relevant reference levels.

SUMMARY OF INVENTION

According to a first aspect, the invention relates to an in vitro method for determining whether a NAFLD patient is at risk or not at risk of NASH, of NASH progression or of severe fibrotic NASH, comprising the steps of:

measuring the level of CHI3L1 in a blood, serum or plasma sample from said patient; and comparing the level of CHI3L1 measured in the sample to reference levels;

wherein a level of CHI3L1 in the sample from the patient, compared to the reference levels is indicative of the risk of NASH, of NASH progression or of severe fibrotic NASH in this patient.

The invention further relates to an in vitro method for determining the progression of NASH, comprising the steps of:

measuring the level of CHI3L1 in a blood, serum or plasma sample from a patient at a first timepoint;

measuring the level of CHI3L1 in a blood, serum or plasma sample from said patient at a later timepoint; and comparing the levels of CHI3L1 measured in the samples to reference levels;

wherein the levels of CHI3L1 in the sample from the patient compared to the reference levels are indicative of the progression of NASH.

In a particular embodiment, the sample is a serum sample. Representative reference levels to which serum CHI3L1 levels can be compared include the following values:

a level of CHI3L1 in the sample lower than 20,000 pg/mL is indicative of a non-NASH patient;

a level of CHI3L1 from 20,000 to 40,000 pg/mL is indicative of a patient at risk of having NASH;

a level of CHI3L1 from 40,000 to 70,000 pg/mL is indicative of a patient with probable NASH;

a level of CHI3L1 level from 70,000 to 100,000 pg/mL is indicative of a patient with probable NASH and significant fibrosis;

a level of CHI3L1 level from 100,000 to 150,000 pg/mL is indicative of a patient with probable NASH and advanced fibrosis;

a level of CHI3L1 level from 150,000 to 220,000 pg/mL is indicative of a patient with probable NASH and severe fibrosis; and a level of CHI3L1 level higher than 220,000 pg/mL is indicative of a patient experiencing NASH and severe fibrosis.

In a particular embodiment, reference levels to which serum CHI3L1 levels can be compared include the following values:

a level of CHI3L1 in the sample lower than 25,000 pg/mL is indicative of a non-NASH patient;

a level of CHI3L1 from 25,000 to 33,000 pg/mL is indicative of a patient at risk of having NASH;

a level of CHI3L1 from 33,000 to 78,000 pg/mL is indicative of a patient with probable NASH;

a level of CHI3L1 level from 78,000 to 95,000 pg/mL is indicative of a patient with probable NASH and significant fibrosis;

a level of CHI3L1 level from 95,000 to 170,000 pg/mL is indicative of a patient with probable NASH and advanced fibrosis;

a level of CHI3L1 level from 170,000 to 215,000 pg/mL is indicative of a patient with probable NASH and severe fibrosis; and a level of CHI3L1 level higher than 215,000 pg/mL is indicative of a patient experiencing NASH and severe fibrosis.

Furthermore, the present invention relates to a method for determining the severity of NASH in a patient, wherein a determined level of CHI3L1 above or below one or more reference levels is indicative of the severity of NASH.

In another aspect, the invention relates to a kit comprising means to implement the method of the invention. In a particular embodiment, the kit comprises means to conduct a CHI3L1 ELISA assay from a blood, serum or plasma sample, in particular a serum sample. Illustrative means include at least one container comprising an antibody specific for CHI3L1 and at least one container comprising recombinant CHI3L1 protein at a known concentration. In a particular embodiment, the at least one container comprising recombinant CHI3L1 protein at a known concentration can be used to prepare at least one control sample comprising CHI3L1 at the concentration of at least one of reference levels described herein. In another embodiment, the at least one container comprises CHI3L1 at a concentration corresponding to at least one of the reference levels described herein.

LEGENDS OF THE FIGURES

FIG. 1: measure of CHI3L1 level at end of study (EOS) of patients diagnosed F0 at the screening visit (SV).

Figure 2:
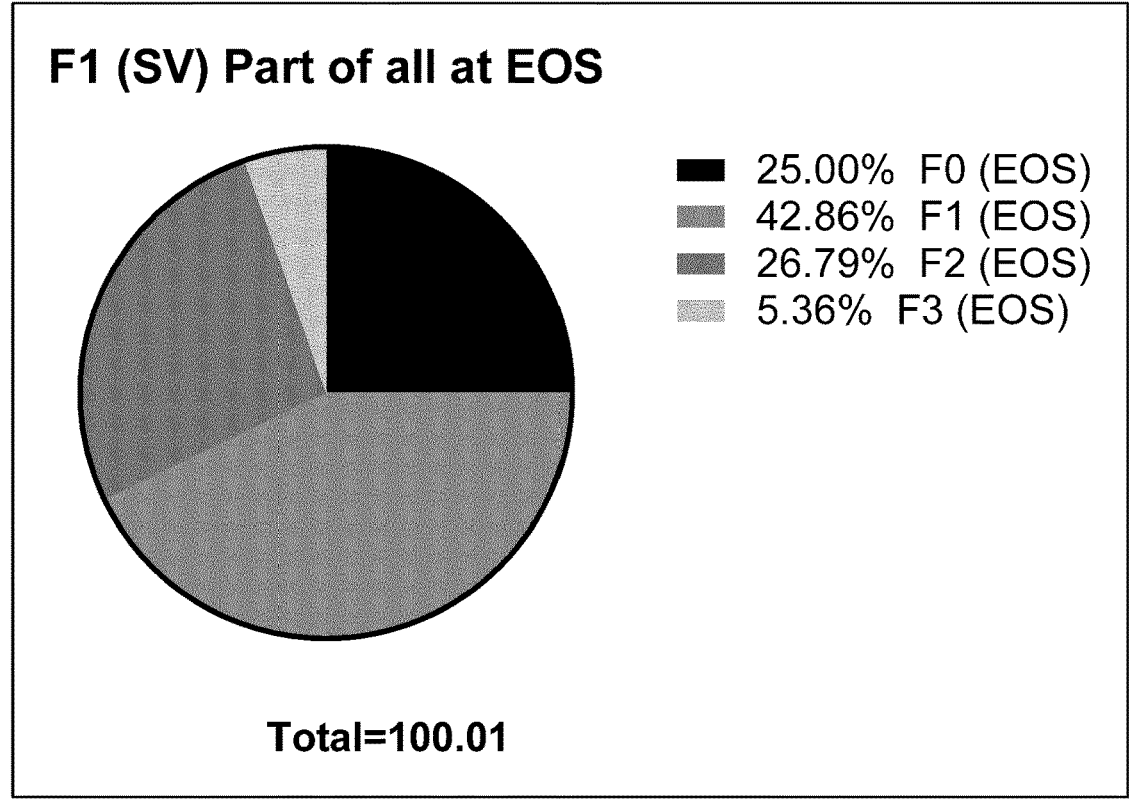

FIG. 2: measure of CHI3L1 level at end of study (EOS) of patients diagnosed F1 at the SV.

Figure 3:
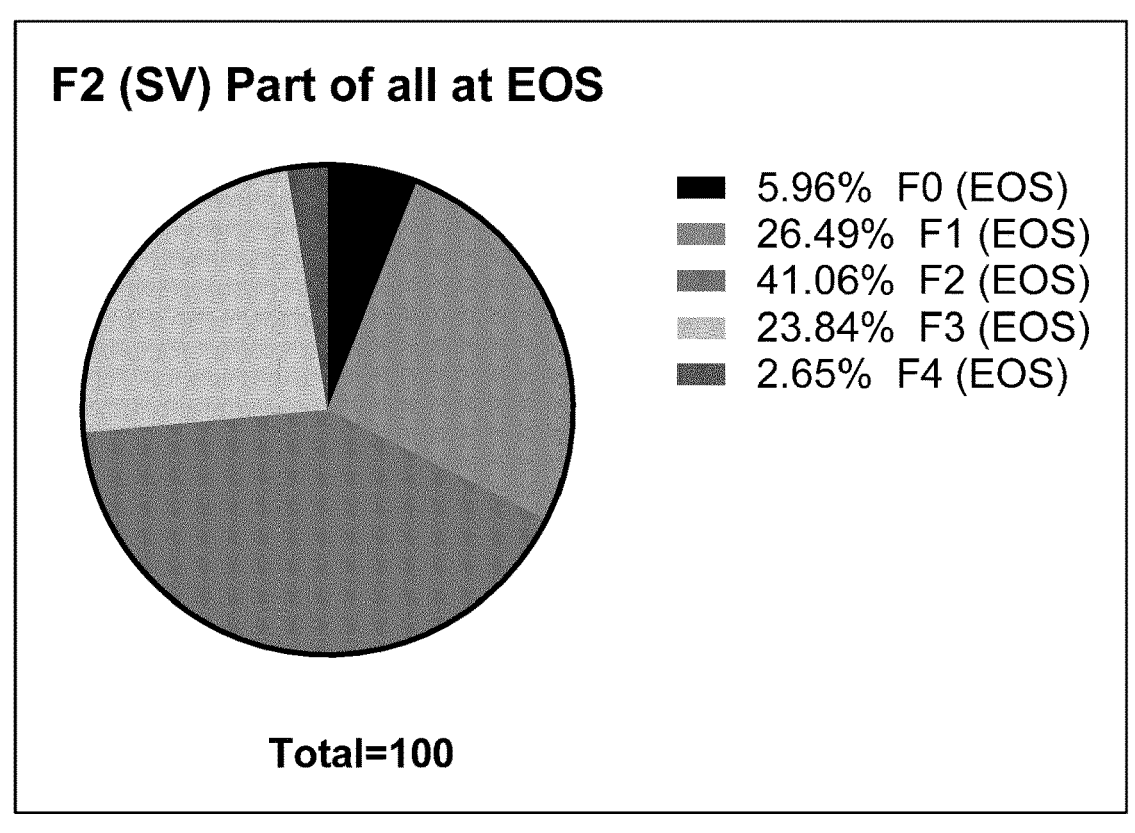

FIG. 3: measure of CHI3L1 level at end of study (EOS) of patients diagnosed F2 at the SV.

Figure 4:
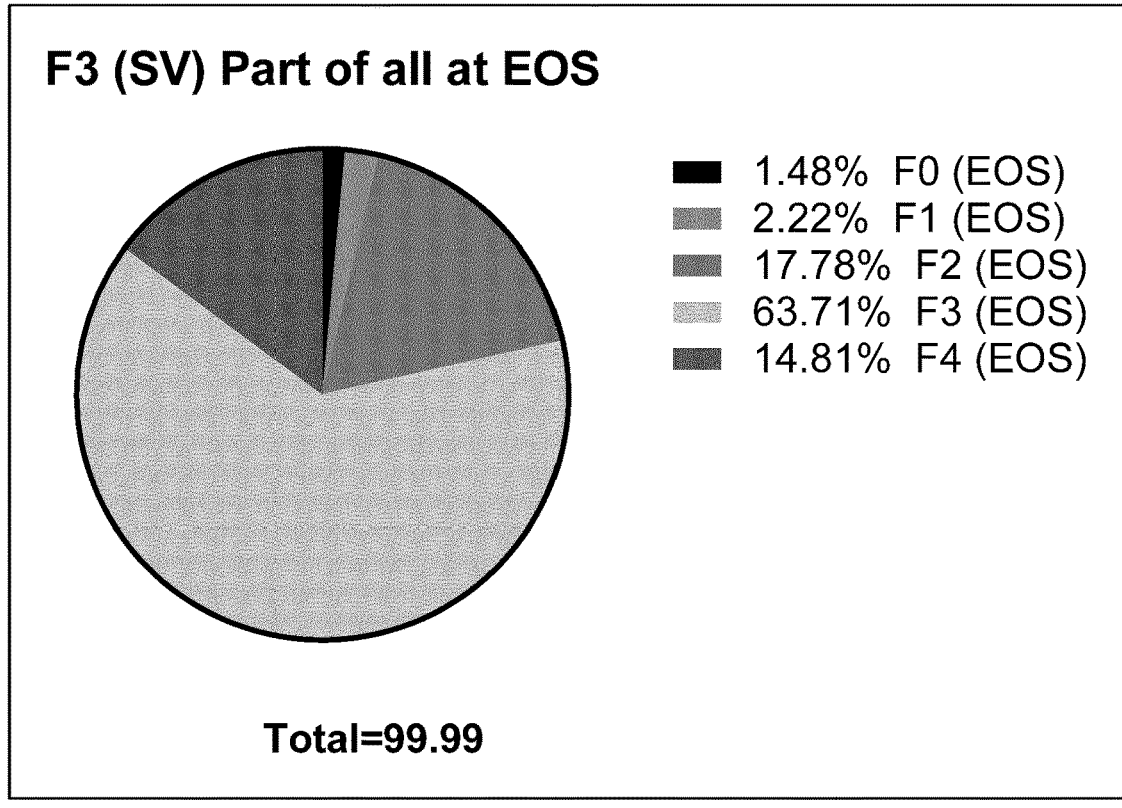

FIG. 4: measure of CHI3L1 level at end of study (EOS) of patients diagnosed F3 at the SV.

DETAILED DESCRIPTION OF THE INVENTION

NASH and Fibrosis Scoring/Staging

Histological scoring/staging systems have been developed to assess NAFLD activity level and fibrosis stage and to estimate the risk of evolution to clinical liver outcomes. The NALFD-Activity-Score (NAS) has been developed to assess the severity of NAFLD. NAS is the sum of three histological scores determined from liver biopsy slices:

S: Steatosis score: 0: <5%; 1: 5-33%; 2: 34-66% and 3: >66%;

LI: Lobular Inflammation score (foci per 20× field): 0: none; 1: <2 foci; 2: 2-4 foci and 3: >4 foci; and HB: Ballooning degeneration score: 0: none; 1: few; 2: many cells/prominent ballooning.

Using this scoring system, a "patient with NASH" has NAS≥3, with at least 1 point in steatosis, at least 1 point in lobular inflammation and at least 1 point in hepatocyte ballooning. A "non-NASH" patient is a patient having either (i) a NAS≥3 with at least one of steatosis, lobular inflammation and hepatocyte ballooning scores equal to 0; or (ii) a NAS<3. In addition, in the context of the present invention, a patient is excluded as being a NASH patient if said patient has viral hepatitis, alcohol-related liver disease, autoimmune liver disease, drug-induced liver disease and congenital causes of chronic liver disease such as hereditary hemochromatosis, Wilson's disease, alpha-1-antitrypsin deficiency and polycystic ovary syndrome.

Localization and extent of fibrosis (F) at histological exam signs the severity (advancement) of NASH. The NASH-CRN (Nonalcoholic SteatoHepatitis Clinical Research Network) has developed a dedicated fibrosis staging system (Kleiner, D. E et al, Hepatology, 2005 June; 41(6):1313-21).

| NASH Clinical Research Network Scoring System Definitions | F Score |
|---|---|
| Perisinusoidal or periportal fibrosis | 1 |
| Mild perisinusoidal fibrosis (zone 3) | 1a |
| Moderate perisinusoidal fibrosis (zone 3) | 1b |
| Portal/periportal fibrosis | 1c |
| Perisinusoidal and portal/periportal fibrosis | 2 |
| Bridging fibrosis | 3 |
| Cirrhosis | 4 |

Using this fibrosis staging system, patients with no or minimal fibrosis (F=0-1) are generally not considered at risk of cirrhosis, HCC (hepatocellular carcinoma) or liver-related death. Patients with significant (F=2) and moderate fibrosis (F=3) are at increasing risk of developing cirrhosis, liver failure, HCC and liver-related death. Patients with compensated cirrhosis have severe fibrosis (F=4) and are at high risk of liver failure (decompensated cirrhosis), HCC and liver-related deaths. Identifying patients who are at risk of developing HCC, cirrhotic complications and liver-related deaths is the ultimate reason for liver assessment. As defined by the FDA and EMA, patients at risk of liver outcomes who should be pharmacologically treated are those with NAS≥4 (with score≥1 for each of steatosis, lobular inflammation and ballooning) and NASH-CRN fibrosis score (F)≥2.

Accordingly, in the context of the present invention:

a "non-NASH" patient is a patient having either (i) a NAS≥3 with at least one of steatosis, lobular inflammation and hepatocyte ballooning scores equal to 0; or (ii) a NAS<3 a NAFLD patient is a patient with at least a S score higher or equal to 1;

a "patient not at risk of NASH progression" is a patient with a NAS higher or equal to 3, a S score higher or equal to 1, a LI score higher or equal to 1, a HB score higher or equal to 1 and a F score of 0 or 1;

a "patient at risk of NASH progression" is a patient with a NAS higher or equal to 4, a S score higher or equal to 1, a LI score higher or equal to 1, a HB score higher or equal to 1 and a F score of 2 or 3;

a "patient with NASH and significant fibrosis" is a patient with a NAS higher or equal to 4, a S score higher or equal to 1, a LI score higher or equal to 1, a HB score higher or equal to 1 and a F score of 2;

a "patient with NASH and advanced fibrosis" is a patient with a NAS higher or equal to 4, a S score higher or equal to 1, a LI score higher or equal to 1, a HB score higher or equal to 1 and a F score of 3;

a "patient with NASH and severe fibrosis" is a patient with a NAS higher or equal to 4, a S score higher or equal to 1, a LI score higher or equal to 1, a HB score higher or equal to 1 and a F score of 4.

CHI3L1 Protein and Detection Thereof

"Chitinase 3-like protein 1" or "CHI3L1" (also known as YKL-40), is a secreted glycoprotein that is approximately 40 kDa in size. In humans, this protein is encoded by the CHI3L1 gene. CHI3L1 is expressed and secreted by various cell-types including macrophages, chondrocytes, fibroblast-like synovial cells, vascular smooth muscle cells, and hepatic stellate cells. The biological function of CHI3L1 is unclear but its pattern of expression is associated with pathogenic processes related to inflammation, extracellular tissue remodeling, fibrosis and solid carcinomas and asthma.

The amino acid sequence of human CHI3L1 is shown in SEQ ID NO:1 (UniProtKB accession number P36222).

It is herein shown that CHI3L1 levels measured from a blood-derived sample from a NASH patient can be advantageously used to determine NASH progression or NASH severity.

Assays to measure the level of CHI3L1 level include, without limitation, mass spectrometry and immunoassays. The level of CHI3L1 can be measured using a CHI3L1-specific binding agent, such as an anti-CHI3L1 antibody. In a particular embodiment, the immunoassay is enzyme-linked immunosorbent assay (ELISA). In this respect, commercial kits for CHI3L1 level determination are readily available, such as the Quantikine® Chitinase 3-like 1 Immunoassay (R&D Systems, Inc.).

Diagnosis of NASH, Determination of the Risk of NASH Progression or NASH Severity The present invention relates to an in vitro method for determining whether a patient is at risk or not at risk of NASH.

Moreover, the present invention relates to an in vitro method for determining whether a patient with NASH is at risk or not at risk of NASH progression.

The present invention further relates to an in vitro method for determining the progression of NASH in a patient.

The present invention also relates to an in vitro method for determining the severity of NASH in a patient with NASH.

The present invention also relates to an in vitro method for assessing the presence of severe fibrosis or F=4 in patients with NASH.

The patient may be any patient who has been identified as having NAFLD, or as potentially having NASH, thanks to a method available to the practitioner.

The method of the present invention is based on the measure of the level of a specific biomarker, the CHI3L1 protein, in a blood, serum or plasma sample of a NAFLD patient, and the comparison of this measured level to reference levels that are provided herein.

In a particular embodiment, the sample is a serum sample.

A first set of reference levels to which serum CHI3L1 levels can be compared include the following values.

According to a particular embodiment, a first reference level of 20,000 pg/mL is used to determine whether the patient has NASH or does not have NASH. A measured CHI3L1 level lower than this first reference level is indicative of the absence of NASH. A measured CHI3L1 level higher than this first reference level is indicative of NASH diagnosis.

According to another embodiment, it is herein provided a reference range level of 20,000 to 40,000 pg/mL. A level of CHI3L1 measured in the sample comprised within this range is indicative of a patient at risk of having NASH.

According to another embodiment, it is herein provided a reference range level of 40,000 to 70,000 pg/mL. A level of CHI3L1 measured in the sample comprised within this range is indicative of a patient with probable NASH.

According to another embodiment, it is herein provided a reference range level of 70,000 to 100,000 μg/mL. A level of CHI3L1 measured in the sample comprised within this range is indicative of a patient with probable NASH and significant fibrosis.

According to another embodiment, it is herein provided a reference range level of 100,000 to 150,000 μg/mL. A level of CHI3L1 measured in the sample comprised within this range is indicative of a patient with probable NASH and advanced fibrosis.

According to another embodiment, it is herein provided a reference range level of 150,000 to 220,000 pg/mL. A level of CHI3L1 measured in the sample comprised within this range is indicative of a patient with probable NASH and severe fibrosis.

According to another embodiment, it is herein provided a reference level of 220,000 pg/mL. A level of CHI3L1 measured in the sample higher than this reference level is indicative of a patient experiencing NASH and severe fibrosis.

A second set of reference levels to which serum CHI3L1 levels can be compared include the following values.

According to a particular embodiment, a first reference level of 25,000 pg/mL is used to determine whether the patient has NASH or does not have NASH. A measured CHI3L1 level lower than this first reference level is indicative of the absence of NASH. A measured CHI3L1 level higher than this first reference level can be indicative of NASH diagnosis.

According to another embodiment, it is herein provided a reference range level of 25,000 to 33,000 pg/mL. A level of CHI3L1 measured in the sample comprised within this range is indicative of a patient at risk of having NASH.

According to another embodiment, it is herein provided a reference range level of 33,000 to 78,000 pg/mL. A level of CHI3L1 measured in the sample comprised within this range is indicative of a patient with probable NASH.

According to another embodiment, it is herein provided a reference range level of 78,000 to 95,000 μg/mL. A level of CHI3L1 measured in the sample comprised within this range is indicative of a patient with probable NASH and significant fibrosis.

According to another embodiment, it is herein provided a reference range level of 95,000 to 170,000 μg/mL. A level of CHI3L1 measured in the sample comprised within this range is indicative of a patient with probable NASH and advanced fibrosis.

According to another embodiment, it is herein provided a reference range level of 170,000 to 215,000 pg/mL. A level of CHI3L1 measured in the sample comprised within this range is indicative of a patient with probable NASH and severe fibrosis.

According to another embodiment, it is herein provided a reference level of 215,000 pg/mL. A level of CHI3L1 measured in the sample higher than this reference level is indicative of a patient experiencing NASH and severe fibrosis.

A third set of reference levels to which serum CHI3L1 levels can be compared include the following values.

According to a particular embodiment, a first reference level of 26,727 pg/mL is used to determine whether the patient has NASH or do not have NASH. A measured CHI3L1 level lower than this first reference level is indicative of the absence of NASH. A measured CHI3L1 level higher than this first reference level is indicative of NASH diagnosis.

According to another embodiment, it is herein provided a reference range level of 26,727 to 31,211 pg/mL. A level of CHI3L1 measured in the sample comprised within this range is indicative of a patient at risk of having NASH.

According to another embodiment, it is herein provided a reference range level of 31,211 to 79,790 pg/mL. A level of CHI3L1 measured in the sample comprised within this range is indicative of a patient with probable NASH.

According to another embodiment, it is herein provided a reference range level of 79,790 to 91,399 pg/mL. A level of CHI3L1 measured in the sample comprised within this range is indicative of a patient with probable NASH and significant fibrosis.

According to another embodiment, it is herein provided a reference range level of 91,399 to 182,880 pg/mL. A level of CHI3L1 measured in the sample comprised within this range is indicative of a patient with probable NASH and advanced fibrosis.

According to another embodiment, it is herein provided a reference range level of 182,880 to 209,604 pg/mL. A level of CHI3L1 measured in the sample comprised within this range is indicative of a patient with probable NASH and severe fibrosis.

According to another embodiment, it is herein provided a reference level of 209,604 pg/mL. A level of CHI3L1 measured in the sample higher than this reference level is indicative of a patient experiencing NASH and severe fibrosis.

Of course, selection of the first, second or third set of reference values will depend on the choice of the skilled person to use large or narrow confidence interval to obtain a diagnosis.

As mentioned above, the invention also relates to an in vitro method for the determination of the progression of NASH. In this embodiment, a first measure of the level of CHI3L1 is carried out in a sample from the patient at a timepoint. Then, at a later timepoint, another measure of the level of CHI3L1 is carried out in another sample from the same patient. The level of CHI3L1 is compared to reference levels at each timepoint, and disease progression is determined based on these measures and their comparisons to said reference levels. Accordingly, thanks to the invention, disease progression can be determined, for example, for:

- progression from no NASH to a risk of NASH;
- progression from no NASH to probable NASH;
- progression from no NASH to probable NASH and significant fibrosis;
- progression from no NASH to probable NASH and advanced fibrosis;
- progression from no NASH to probable NASH and severe fibrosis;
- progression from no NASH to NASH and severe fibrosis;
- progression from a risk of NASH to probable NASH;
- progression from a risk of NASH to probable NASH and significant fibrosis;
- progression from a risk of NASH to probable NASH and advanced fibrosis;
- progression from a risk of NASH to probable NASH and severe fibrosis;
- progression from a risk of NASH to NASH and severe fibrosis;
- progression from probable NASH to probable NASH and significant fibrosis;
- progression from probable NASH to probable NASH and advanced fibrosis;
- progression from probable NASH to probable NASH and severe fibrosis;
- progression from probable NASH to NASH and severe fibrosis;
- progression from probable NASH with significant fibrosis to probable NASH and advanced fibrosis;
- progression from probable NASH with significant fibrosis to probable NASH and severe fibrosis;
- progression from probable NASH with significant fibrosis to NASH and severe fibrosis;
- progression from probable NASH with advanced fibrosis to probable NASH and severe fibrosis;
- progression from probable NASH with advanced fibrosis to NASH and severe fibrosis; or
- progression from probable NASH with severe fibrosis to NASH and severe fibrosis.

In addition to the level of CHI3L1, the level of other markers of NASH, NASH severity or liver fibrosis can be measured. Illustrative additional markers include, without limitation, hsa-miR-34a-5p, alpha-2-macroglobulin, and HbA1c.

In a particular embodiment, the information obtained thanks to the invention can be further confirmed with other assays. For example, after detection of the patient as being at risk of NASH progression or as having NASH with severe fibrosis, a liver biopsy can be carried out to confirm this finding. The method of the present invention can thus be advantageously used to avoid practicing liver biopsy on patients who do not have NASH, or not at risk of NASH progression.

Kits of the Invention

The invention further relates to a kit that includes means suitable to specifically measure CHI3L1 levels. The kit of the invention can further include other means suitable to measure other markers related to NASH, NASH severity or liver fibrosis. In particular, the other biomarker is hsa-miR-34a-5p.

In a particular embodiment, the kit comprises means to conduct a CHI3L1 ELISA assay from a blood, serum or plasma sample, in particular a serum sample. Illustrative means include at least one container comprising an antibody specific for CHI3L1 and at least one container comprising recombinant CHI3L1 protein at a known concentration. In a particular embodiment, the at least one container comprising recombinant CHI3L1 protein at a known concentration can be used to prepare at least one control sample comprising CHI3L1 at the concentration of at least one of the reference levels described herein. In another embodiment, the at least one container comprising CHI3L1 at a concentration corresponding to at least one of the reference levels described herein.

In yet another embodiment, the kit of the invention comprises at least one container suitable to generate a CHI3L1 calibration curve within a range relevant to the method of the present invention. The at least one container is useful in that the level of CHI3L1 in said containers can be measured along the level of CHI3L1 within the test sample(s), to compensate analytical variability.

In a particular embodiment, the kit of the invention comprises at least one container comprising recombinant CHI3L1 protein at a concentration comprised between 15,000 and 275,000 pg/mL. In a further particular embodiment, the kit comprises at least two containers each comprising recombinant CHI3L1 protein at a concentration comprised between 15,000 and 275,000 pg/mL, wherein the concentration of recombinant CHI3L1 protein is different within each container.

In another particular embodiment, the kit of the invention comprises at least one container comprising recombinant CHI3L1 protein at a concentration comprised between 20,000 and 220,000 µg/mL. In a further particular embodiment, the kit comprises at least two containers each comprising recombinant CHI3L1 protein at a concentration comprised between 20,000 and 220,000 µg/mL, wherein the concentration of recombinant CHI3L1 protein is different within each container.

In a particular embodiment, the kit of the invention comprises at least one container comprising recombinant CHI3L1 protein at a concentration comprised between 25,000 and 215,000 µg/mL. In a further particular embodiment, the kit comprises at least two containers each comprising recombinant CHI3L1 protein at a concentration comprised between 25,000 and 215,000 µg/mL, wherein the concentration of recombinant CHI3L1 protein is different within each container.

In a particular embodiment, the kit of the invention comprises at least one container comprising recombinant CHI3L1 protein at a concentration comprised between 26,727 and 209,604 pg/mL. In a further particular embodiment, the kit comprises at least two containers each comprising recombinant CHI3L1 protein at a concentration comprised between 26,727 and 209,604 pg/mL, wherein the concentration of recombinant CHI3L1 protein is different within each container.

In a particular embodiment, the kit of the invention comprises at least one container selected in the group consisting of:

a container comprising recombinant CHI3L1 protein at a concentration of 20,000 pg/mL;

a container comprising recombinant CHI3L1 protein at a concentration of 40,000 pg/mL;

a container comprising recombinant CHI3L1 protein at a concentration of 70,000 pg/mL;

a container comprising recombinant CHI3L1 protein at a concentration of 100,000 pg/mL;

a container comprising recombinant CHI3L1 protein at a concentration of 150,000 pg/mL; and a container comprising recombinant CHI3L1 protein at a concentration of 220,000 pg/mL.

In another embodiment, the kit of the invention comprises at least two containers selected from:

a container comprising recombinant CHI3L1 protein at a concentration of 20,000 pg/mL;

a container comprising recombinant CHI3L1 protein at a concentration of 40,000 pg/mL;

a container comprising recombinant CHI3L1 protein at a concentration of 70,000 pg/mL;

a container comprising recombinant CHI3L1 protein at a concentration of 100,000 pg/mL;

a container comprising recombinant CHI3L1 protein at a concentration of 150,000 pg/mL; and a container comprising recombinant CHI3L1 protein at a concentration of 220,000 pg/mL.

In another embodiment, the kit of the invention comprises all the following containers:

a container comprising recombinant CHI3L1 protein at a concentration of 20,000 pg/mL;

a container comprising recombinant CHI3L1 protein at a concentration of 40,000 pg/mL;

a container comprising recombinant CHI3L1 protein at a concentration of 70,000 pg/mL;

a container comprising recombinant CHI3L1 protein at a concentration of 100,000 pg/mL;

a container comprising recombinant CHI3L1 protein at a concentration of 150,000 pg/mL; and a container comprising recombinant CHI3L1 protein at a concentration of 220,000 pg/mL.

In a particular embodiment, the kit of the invention comprises at least one container selected in the group consisting of:

a container comprising recombinant CHI3L1 protein at a concentration of 25,000 pg/mL;

a container comprising recombinant CHI3L1 protein at a concentration of 33,000 pg/mL;

a container comprising recombinant CHI3L1 protein at a concentration of 78,000 pg/mL;

a container comprising recombinant CHI3L1 protein at a concentration of 95,000 pg/mL;

a container comprising recombinant CHI3L1 protein at a concentration of 170,000 pg/mL; and a container comprising recombinant CHI3L1 protein at a concentration of 215,000 pg/mL.

In another embodiment, the kit of the invention comprises at least two containers selected from:

a container comprising recombinant CHI3L1 protein at a concentration of 25,000 pg/mL;

a container comprising recombinant CHI3L1 protein at a concentration of 33,000 pg/mL;

a container comprising recombinant CHI3L1 protein at a concentration of 78,000 pg/mL;

a container comprising recombinant CHI3L1 protein at a concentration of 95,000 pg/mL;

a container comprising recombinant CHI3L1 protein at a concentration of 170,000 pg/mL; and a container comprising recombinant CHI3L1 protein at a concentration of 215,000 pg/mL.

In another embodiment, the kit of the invention comprises all the following containers:

a container comprising recombinant CHI3L1 protein at a concentration of 25,000 pg/mL;

a container comprising recombinant CHI3L1 protein at a concentration of 33,000 pg/mL;

a container comprising recombinant CHI3L1 protein at a concentration of 78,000 pg/mL;

a container comprising recombinant CHI3L1 protein at a concentration of 95,000 pg/mL;

a container comprising recombinant CHI3L1 protein at a concentration of 170,000 pg/mL; and a container comprising recombinant CHI3L1 protein at a concentration of 215,000 pg/mL.

In a particular embodiment, the kit of the invention comprises at least one container selected in the group consisting of:

a container comprising recombinant CHI3L1 protein at a concentration of 26,727 pg/mL;

a container comprising recombinant CHI3L1 protein at a concentration of 31,211 pg/mL;

a container comprising recombinant CHI3L1 protein at a concentration of 79,790 pg/mL;

a container comprising recombinant CHI3L1 protein at a concentration of 91,399 pg/mL;

a container comprising recombinant CHI3L1 protein at a concentration of 182,880 pg/mL; and a container comprising recombinant CHI3L1 protein at a concentration of 209,604 pg/mL.

In another embodiment, the kit of the invention comprises at least two containers selected from:

a container comprising recombinant CHI3L1 protein at a concentration of 26,727 pg/mL;

a container comprising recombinant CHI3L1 protein at a concentration of 31,211 pg/mL;

a container comprising recombinant CHI3L1 protein at a concentration of 79,790 pg/mL;

a container comprising recombinant CHI3L1 protein at a concentration of 91,399 pg/mL;

a container comprising recombinant CHI3L1 protein at a concentration of 182,880 pg/mL; and a container comprising recombinant CHI3L1 protein at a concentration of 209,604 pg/mL.

In another embodiment, the kit of the invention comprises all the following containers:

a container comprising recombinant CHI3L1 protein at a concentration of 26,727 pg/mL;

a container comprising recombinant CHI3L1 protein at a concentration of 31,211 pg/mL;

a container comprising recombinant CHI3L1 protein at a concentration of 79,790 pg/mL;

a container comprising recombinant CHI3L1 protein at a concentration of 91,399 pg/mL;

a container comprising recombinant CHI3L1 protein at a concentration of 182,880 pg/mL; and a container comprising recombinant CHI3L1 protein at a concentration of 209,604 pg/mL.

EXAMPLES

Example 1: ELISA Assay to Classify NASH Patients at Risk or not at Risk of Progression 1. Patients Characteristics GOLDEN-505 Cohort (NCT01694849)

Patients were recruited in the United States (US) and European countries. According to histological inclusion criteria, patients were eligible to participate in the interventional trial if a liver biopsy collected during the time of screening showed presence of NASH with a [NAS] with point in each of steatosis, lobular inflammation and hepatocyte ballooning scores, with or without fibrosis. Blood samples were collected prior to intervention for standard haematological and biochemical analyses.

RESOLVE-IT-DIAG Cohort (NCT02704403)

Patients were recruited at global centers (US, Latin America, Central America, and Europe). A liver biopsy was collected for all patients, and all biopsy samples were centrally read by an expert pathologist. Blood samples were collected prior to intervention for standard haematological and biochemical analyses.

Haematology and biochemical analyses were performed by the central laboratory of GOLDEN-505 and RESOLVE-IT™ trials (BARC-Europe, Ghent, Belgium) under fasting conditions.

The demographic and baseline characteristics of cohorts are described in Table 1. The distribution of fibrosis stage was similar across cohorts. Patients without fibrosis (F0) or with early fibrosis (F1) represented 41%-51% of patients across cohorts.

ALT: alanine transaminase; AST: aspartate transaminase; IU: international unit; SD: standard deviation; NAS: nonalcoholic fatty liver disease activity score.

2. Preparation of a Low, Medium and High Positive Control.

Human CHI3L1 lyophilized standard was obtained from R&D Systems and a pool of healthy human serum was obtained from Bio-Rad (matrix #1 Bio-Rad). A low positive control (corresponding to calculated mean value in non-NASH subjects) was prepared with Bio-Rad matrix #1 and CHI3L1. A medium positive control (corresponding to the mean value in subjects with NASH, NAS=4 and F=2) was set according to approximate medical decision cut-off for NIS4™. A high positive control was set according to average value observed in patients with NASH and severe fibrosis (i.e. corresponding to the mean value measured in patients with NASH and severe fibrosis). The dilution was performed in Bio-Rad matrix #1. The three positive controls (low, medium and high) were aliquoted and stored at $-80°$ C. until use.

3. CHI3L1 Level Quantification in Serum Samples and Standard Positive Controls.

Positive controls were processed similarly to serum samples and assayed in duplicate using manufacturer's procedure (Quantikine® ELISA Human Chitinase 3-like 1 Immunoassay Kit (RUO), DC3L10, R&D Systems, Minneapolis, USA) and with automation. Washing steps were performed with the Tecan HydroSpeed™ plate washer (Tecan, Männedorf, ref. 30054550 Switzerland), the reading was determined using Thermo Scientific™ Multiskan™ GO Microplate Spectrophotometer (ThermoFisher, ref. 51119200 Massachusetts, USA) set to 450 nm.

Data analyses were carried out by calculating the average of duplicate readings for each standard, control, and sample and subtract the average zero standard density.

Range limits of each lot of positive controls were established for use in each CHI3L1 assay run validity. Range limits were determined by assaying each control of the new lot over replicates splitted in 5 runs of 6 replicates each. Target concentration for each positive control was deter-

TABLE 1

Patient characteristics of independent cohorts.

| | GOLDEN-505 | RESOLVE-IT-DIAG | TOTAL |
|---|---|---|---|
| N | 239 | 475 | 714 |
| Sex, male, % | 54 | 45 | 48 |
| Age (years), mean ± SD | 52 ± 12 | 55 ± 12 | 54 ± 12 |
| ALT (IU/L), mean ± SD | 63.59 ± 41.2 | 64 ± 43.9 | 63.88 ± 42.99 |
| AST (IU/L), mean ± SD | 42.79 ± 26.63 | 45.97 ± 29.8 | 44.91 ± 28.81 |
| Patients with At risk NASH, % | 43.5 | 54.7 | 51.0 |
| Fibrosis stage, % | | | |
| F = 0 | 15 | 12 | 13 |
| F = 1 | 36 | 29 | 31 |
| F = 2 | 27 | 28 | 28 |
| F = 3 | 22 | 29 | 27 |
| F = 4 | 0 | 2 | 1 |
| NAS category, % | | | |
| 0-1 | 0 | 8 | 5 |
| 2-3 | 13 | 10 | 11 |
| 4-5 | 52 | 48 | 49 |
| ≥6 | 35 | 34 | 35 | mined as mean value across all runs. High and low Limit concentrations were determined by 2 standard deviations calculated on all the points measured. Each control was tested in thirty-four separate assays (duplicate) to assess the acceptable range (±2 SD).

4. Results

CHI3L1 levels were measured on 714 patients from GOLDEN-505 and RESOLVE-IT™ drug trials.

TABLE 2

Average values of CHI3L1 in NASH diseased
patients from clinical studies.

| Fibrosis stage | 0 | 1 | 2 | 3 | 4 |
|---|---|---|---|---|---|
| Mean NAS | 3.4 | 4.4 | 5.4 | 5.4 | 3.4 |
| Mean (pg/ml) | 42 386 | 58 244 | 80 802 | 136 598 | 144 712 |
| SEM | 2 858 | 2 825 | 4 750 | 13 042 | 59 272 |
| Fibrosis stage | 0 | 1 | 2 | 3 | 4 |

SEM: standard error mean.
SEM = SD/√n.
n: number of patients in each category.

The assessment of CHI3L1 in NASH patients showed that NASH patients without fibrosis had CHI3L1 mean levels of 42 386 pg/mL plus or minus 2 858 pg/mL. NASH patients with a fibrosis stage of 1 had CHI3L1 mean levels of 58 244 pg/mL plus or minus 2 825 pg/mL. Both categories F=0 or F=1 represented NASH patients not at risk of developing NASH complications. NASH patients at risk had CHI3L1 mean levels of 80 802 pg/mL plus or minus 4 750 pg/mL with F=2, 136 598 pg/mL plus or minus 13 042 pg/mL with F=3 and 144 712 pg/mL plus or minus 59 272 pg/mL with F=4 (Table 2).

TABLE 3

Determination of positive control ranges.

| CHI3L1 | Assay n = 34 | | | | | |
|---|---|---|---|---|---|---|
| (pg/mL) | Mean | SD | CV % | 2SD | MIN | MAX |
| Low positive | 28 969 | 1 120.9 | 3.9 | 2241.7 | 26 727 | 31 211 |
| Medium positive | 85 594 | 2 902.3 | 3.4 | 5804.6 | 79 790 | 91 399 |
| High positive | 196 242 | 6 681.0 | 3.4 | 13362.1 | 182 880 | 209 604 |

SD: standard deviation, CV: coefficient of variability, minimum (MIN) and maximum (MAX) acceptable values.

The positive standard controls range from about 30 000 up to about 200 000 pg/mL and cover the whole range of CHI3L1 levels in NASH patients from Golden-Diag and Resolve-it-Diag cohorts prior to any active drug treatment The low positive control was determined at 28 969 pg/ml with an acceptance range from 26 727 to 31 211 pg/ml. This level is used to diagnose NASH patients among healthy individuals. The medium positive control was determined at 85 594 pg/ml with an acceptance range from 79 790 to 91

399 pg/ml. This level is used to diagnose NASH patients at risk of progression. The high positive control was determined at 196 242 pg/ml with an acceptance range from 182 880 to 209 604 pg/ml. This level is used to diagnose severe fibrotic NASH disease.

Coefficient of Variability is calculated by dividing the standard deviation (SD) of a set of measurements by the mean of the set, which is then expressed as a percentage of variation to the mean. The low coefficient of variability (CV %<5%) between sample replicates demonstrated that the assay was well-run and the resultant data was precise and accurate.

CHI3L1 quantification results with this assay are robust and stable and allow the diagnosis, the monitoring and stratification of NASH patients at risk of progression towards a more severe form of NASH or patients to be treated.

Example 2: Levels of CHI3L1 Protein in Patient Samples at Different Times

The method of the present invention is based on the measure of the level of the CHI3L1 protein, in a sample of a NAFLD patient, and the comparison of this measured level to reference levels to estimate the fibrosis score.

The levels of the CHI3L1 protein have been assessed in different populations from the RESOLVE-IT study (431 patients) at the first visit of the patients (SV visit—screening visit) and at the end of the study (EOS) visit, 72 weeks after the SV.

Several groups of patients were defined according to their fibrosis status at the SV as determined by the method according to the invention. Their fibrosis status was then checked at the EOS visit with the method according to the invention, and with liver biopsies. Both method correlated.

The results are shown in FIGS. 1 to 4.

In FIG. 1, the major part of patients diagnosed F0 at SV remained stable at EOS visit (57.6%); 30% progressed to F1 and 12% to F2 with no one progressing to the highest stage of fibrosis, F3 and F4.

In FIG. 2, 43% of F1 patients at SV remained stable at EOS, 25% improved their histology to F0 and 26.8% worsened to F2. Only 5.4% worsened to F3 and no patient shifted to F4 stage.

In FIG. 3, 41% of F2 patients at SV remained stable at EOS, 6% and 26% improved their hepatic fibrosis to F0 and F1 stages at EOS, respectively. 23.8% and 2.6% worsened to F3 and F4 at EOS visit, respectively.

FIG. 4 shows that the major part of patients diagnosed F3 at SV remained stable at this hepatic fibrosis stage at EOS visit (around 64%). The number of patients that improved their hepatic fibrosis was weak (1.5% F0, 2.2% F1 and 17.8% F2) and around 15% of F3 patients at SV worsened to F4 stage.

Taken together, these results show the progression of patients between the different fibrosis stages. Indeed, these results show that the diagnostic method of the invention is able to determine whether a patient with NASH is at risk or not at risk of NASH progression.

The invention claimed is:

1. An in vitro method for diagnosing whether a nonalcoholic fatty liver disease (NAFLD) patient is at risk or not at risk of nonalcoholic steatohepatitis (NASH), of NASH progression or of severe fibrotic NASH, or an in vitro method for determining the progression of NASH, comprising the steps of:

measuring the level of CHI3L1 in a blood, serum or plasma sample from said patient, said measuring comprising contacting said blood, serum or plasma sample with an antibody specific for CHI3L1 to measure CHI3L1 levels in said blood, serum or plasma samples; and comparing the level of CHI3L1 measured in the sample to reference levels;

wherein a level of CHI3L1 in the sample from the patient compared to the reference levels is indicative of the risk of NASH, of NASH progression or of the fibrosis stage of NASH, or of the progression of NASH, wherein a measured CHI3L1 level lower than 26,727 pg/mL is indicative of a non-NASH patient;

a measured CHI3L1 level from 26,727 to 31,211 pg/mL is indicative of a patient at risk of having NASH;

a measured CHI3L1 level from 31,211 to 79,790 pg/mL is indicative of a patient with probable NASH;

a measured CHI3L1 level from 79,790 to 91,399 pg/mL is indicative of a patient with probable NASH and significant fibrosis (F=2);

a measured CHI3L1 level from 91,399 to 182,800 μg/mL is indicative of a patient with probable NASH and advanced fibrosis (F=3);

a measured CHI3L1 level from 182,800 to 209,604 pg/mL is indicative of a patient with probable NASH and severe fibrosis (F=4); and a measured CHI3L1 level higher than 209,604 pg/mL is indicative of a patient experiencing NASH and severe fibrosis (F=4).

2. The method according to claim 1, wherein the sample is a serum sample.

3. A kit comprising at least one container comprising recombinant CHI3L1 protein at a concentration comprised between 26,727 and 209,604 pg/mL, wherein the kit is configured to be used in the method of claim 1.

4. The kit according to claim 3, comprising at least one container selected from the group consisting of:

a container comprising recombinant CHI3L1 protein at a concentration of 26,727 pg/mL;

a container comprising recombinant CHI3L1 protein at a concentration of 31,211 pg/mL;

a container comprising recombinant CHI3L1 protein at a concentration of 79,790 pg/mL;

a container comprising recombinant CHI3L1 protein at a concentration of 91,399 pg/mL;

a container comprising recombinant CHI3L1 protein at a concentration of 182,880 pg/mL; and a container comprising recombinant CHI3L1 protein at a concentration of 209,604 pg/mL.

5. The kit according to claim 3, comprising at least two containers selected from the group consisting of:

a container comprising recombinant CHI3L1 protein at a concentration of 26,727 pg/mL;

a container comprising recombinant CHI3L1 protein at a concentration of 31,211 pg/mL;

a container comprising recombinant CHI3L1 protein at a concentration of 79,790 pg/mL;

a container comprising recombinant CHI3L1 protein at a concentration of 91,399 pg/mL;

a container comprising recombinant CHI3L1 protein at a concentration of 182,880 pg/mL; and a container comprising recombinant CHI3L1 protein at a concentration of 209,604 pg/mL.

6. The kit according to claim 3, comprising all the following containers:

a container comprising recombinant CHI3L1 protein at a concentration of 26,727 pg/mL;

a container comprising recombinant CHI3L1 protein at a concentration of 31,211 pg/mL;

a container comprising recombinant CHI3L1 protein at a concentration of 79,790 pg/mL;

a container comprising recombinant CHI3L1 protein at a concentration of 91,399 pg/mL;

a container comprising recombinant CHI3L1 protein at a concentration of 182,880 pg/mL; and a container comprising recombinant CHI3L1 protein at a concentration of 209,604 pg/mL.

* * * * *